United States Patent
Dwyer (10) Patent No.: US 10,591,375 B2
(45) Date of Patent: Mar. 17, 2020

(54) PRESSURE SENSOR AND DEVICE COMPRISING THE SAME

(71) Applicant: Frequency Precision Ltd., London (GB)

(72) Inventor: Thomas Dwyer, London (GB)

(73) Assignee: Frequency Precision Ltd. (GB)

(*) Notice: Subject to any disclaimer, the term of this patent is extended or adjusted under 35 U.S.C. 154(b) by 99 days.

(21) Appl. No.: 15/544,167

(22) PCT Filed: Jan. 18, 2016

(86) PCT No.: PCT/GB2016/050100
§ 371 (c)(1),
(2) Date: Jul. 17, 2017

(87) PCT Pub. No.: WO2016/116737
PCT Pub. Date: Jul. 28, 2016

(65) Prior Publication Data
US 2018/0266905 A1    Sep. 20, 2018

(30) Foreign Application Priority Data
Jan. 19, 2015 (GB) .................................. 1500846.9

(51) Int. Cl.
*G01L 9/00* (2006.01)
*A61B 5/11* (2006.01)
(Continued)

(52) U.S. Cl.
CPC ............... *G01L 9/008* (2013.01); *A61B 5/11* (2013.01); *A61B 5/6887* (2013.01); *G01L 19/02* (2013.01);
(Continued)

(58) Field of Classification Search
CPC ........ G01L 9/008; G01L 19/02; G01L 19/148
See application file for complete search history.

(56) References Cited

U.S. PATENT DOCUMENTS 4,456,013 A * 6/1984 De Rossi ........... A61B 5/02156
600/488
4,974,117 A 11/1990 Irwin
(Continued)

FOREIGN PATENT DOCUMENTS

DE    102011054732 A1    4/2013
GB    2043907 A          10/1980
(Continued)

OTHER PUBLICATIONS

International Search Report, PCT/GB2016/0520100 dated Jul. 1, 2016, 6 pages.
(Continued)

*Primary Examiner* — Blake A Tankersley
(74) *Attorney, Agent, or Firm* — Christopher McKeon; Jason Saunders; Arnold & Saunders, LLP (57) ABSTRACT

A pressure sensor is provided, the sensor comprising an inlet for connecting to a body of gas; a diaphragm assembly comprising a first diaphragm and a second diaphragm, the first and second diaphragms defining a chamber therebetween, the chamber being connected to the inlet; a first transducer responsive to movement of the first diaphragm and operable to produce a first electrical signal in response to the same; and a second transducer responsive to movement of the second diaphragm and operable to produce a second electrical signal in response to the same; and an amplifier disposed in the chamber of the diaphragm assembly and connected to the first and second transducers to receive the first and second electrical signals therefrom. A movement sensor assembly for detecting movement of a person is also provided, the assembly comprising a flexible vessel containing a body of gas and a pressure sensor according to any preceding claim, the sensor being arranged to detect changes in the pressure of the gas within the flexible vessel.

16 Claims, 5 Drawing Sheets

(51) Int. Cl.
*G01L 19/02* (2006.01)
*G01L 19/14* (2006.01)
*A61B 5/00* (2006.01)

(52) U.S. Cl.
CPC .......... *G01L 19/148* (2013.01); *A61B 5/6892* (2013.01); *A61B 2562/0247* (2013.01)

(56) References Cited

U.S. PATENT DOCUMENTS

| | | | |
|---|---|---|---|
| 5,363,452 A * | 11/1994 | Anderson | H04R 19/04 |
| | | | 381/170 |
| 5,396,803 A | 3/1995 | Ferran | |
| 6,719,708 B1 | 4/2004 | Jansen | |
| 7,048,697 B1 | 5/2006 | Mitsuru | |
| 7,360,429 B1 | 4/2008 | Filippelli | |
| 2005/0229710 A1 | 10/2005 | O'Dowd et al. | |
| 2014/0100415 A1 | 4/2014 | Hellmuth et al. | |

FOREIGN PATENT DOCUMENTS

| | | |
|---|---|---|
| JP | S6177733 A | 4/1986 |
| WO | 2004018986 A1 | 3/2004 |
| WO | 2004073577 A1 | 9/2004 |

OTHER PUBLICATIONS

Patent Act 1977: Search Report under Section 17 dated Jul. 13, 2015, Application No. GB1500846.9, 2 pages.

* cited by examiner

PRESSURE SENSOR AND DEVICE COMPRISING THE SAME

The present invention relates to a pressure sensor for detecting and measuring the pressure of a gas, such as air. The present invention also relates to a device comprising the pressure sensor.

Pressure sensors are employed in a wide range of applications for measuring the pressure of gases, such as air. One use for an air pressure sensor is in a device for detecting and/or measuring the movements of a person. Such devices are known in the art and are commercially available. In general, the movement of a person is detected by measuring changes in pressure in a volume of air retained in a flexible vessel in contact with the person.

U.S. Pat. No. 6,719,708 concerns a device and method for measuring values form a person lying down and to a pressure sensor. The device comprises a sensor cushion containing a body of air. The sensor cushion may be filled with an elastic material, for example a foam. The device further comprises a sensor element for sensing changes in the air pressure within the cushion. The sensor element may disposed within the cushion or, more preferably, connected to the cushion by way of a hose or flexible capillary. The device may be used to detect movement of a person lying on or in contact with the cushion.

WO 2004/073577 discloses a pad. The pad is for placing under a mattress or cushion, or for direct contact with a person. The pad comprises a plurality of channels containing air at atmospheric pressure. The channels are arranged and of a form to maximise fluctuations in the pressure of air within the channels arising from movements of the person. The channels are connected to a housing containing a pressure sensor and controls for the device. The housing may also comprise a micro-controller to analyse different movements detected by the pressure sensor and distinguish between movements of the person, such as large and small body movements.

More recently, U.S. Pat. No. 7,048,697 discloses a biological information collecting device. The device comprises a closed pneumatic sound sensor. The device is provided with a closed compartment containing air. The closed compartment may be provided with a spring member. A pipe connects the interior of the closed compartment to a non-directional microphone or pressure sensor, by means of which changes in the air pressure within the closed compartment are detected.

In devices such as those of the prior art discussed above, it is important to employ a sensitive pressure sensor, in particular if small movements of the person are to be detected, such as movements arising from the person breathing or from the pulse of the person. One form of pressure sensor comprises a diaphragm for contacting by the gas to be measured. Fluctuations in the gas pressure result in movement of the diaphragm. Such movement is detected by an electrical transducer connected to the diaphragm and operable to convert movement of the diaphragm into an electrical signal. Such diaphragm pressure sensors are known in the art.

Examples of known pressure sensors are described and shown in U.S. Pat. No. 4,974,117, DE 102011054732, GB 2043907, WO 2004/018986 and JPS6177733.

The amplitude of the electrical signal generated by the transducer is determined, in large part, by the extent of movement of the diaphragm. As a result, small fluctuations in the pressure of the gas in contact with the diaphragm result in electrical signals of only a very low amplitude. Such weak electrical signals require amplifying before being further processed. Such a situation can arise when attempting to use a sensing device of the general type described above to detect and measure small movements of a person, in particular to detect and monitor their respiration and heartbeat.

There is a need for an improved diaphragm pressure sensor. In particular, there is a need for a diaphragm pressure sensor that can produce an amplified electrical signal indicative of small fluctuations in gas pressure with reduced noise.

An improved diaphragm pressure sensor has now been found.

According to a first aspect of the present invention, there is provided a pressure sensor comprising:
an inlet for connecting to a body of gas;
a diaphragm assembly comprising:
  a first diaphragm and a second diaphragm, the first and second diaphragms defining a chamber therebetween, the chamber being connected to the inlet;
  a first transducer responsive to movement of the first diaphragm and operable to produce a first electrical signal in response to the same; and
  a second transducer responsive to movement of the second diaphragm and operable to produce a second electrical signal in response to the same; and
an amplifier disposed in the chamber of the diaphragm assembly and connected to the first and second transducers to receive the first and second electrical signals therefrom.

The sensor of the present invention provides a number of significant advantages. First, by employing a diaphragm assembly having two diaphragms, the effects of different orientations and the acceleration due to movement of the sensor are eliminated. Due to the inherent mass of the diaphragm, flexing of the diaphragm in a diaphragm pressure sensor occurs due to gravity. As a consequence, the signal output of the sensor is affected by the orientation of the sensor. In addition, flexing of the diaphragm occurs as a result of acceleration when the sensor is moved. Again, such movement affects the signal output by the sensor. By employing two diaphragms, the aforementioned effects due to orientation and movement may be negated, resulting in the signal output by the sensor being more representative of fluctuations in the gas pressure.

Further, by locating the amplifier in the cavity in the diaphragm assembly between the two diaphragms, the diaphragms may be used to shield the amplifier. In general, the electrical output of the sensor is susceptible to noise arising from electrical and magnetic fields generated by power cables and electrical equipment. It has been found that the first and second diaphragms may be used to shield the amplifier fro such fields, in turn significantly reducing the noise present in the output signal of the sensor.

Still further, by employing two diaphragms, with the chamber therebetween connected to the gas inlet, any fluctuation in the gas pressure within the chamber causes a flexing of both diaphragms, with the first diaphragm flexing in the opposite direction to the second diaphragm. In this way, the electrical signal generated as a result of fluctuations in the gas pressure is increased, compared with the equivalent arrangement employing a single diaphragm. In particular, by selecting the diaphragms to flex the same amount in response to a give change in gas pressure, the electrical signal may be doubled.

The sensor of the present invention comprises an inlet for a gas. In use, the inlet may be connected to a source or body of gas the pressure of which is to be measured. Alternatively, the inlet may be connected to an ambient gas, such as ambient air, with the gas to be measured provided to the external surface of the diaphragms of the sensor.

The sensor is suitable for detecting fluctuations in the pressure of any gas, in particular air. Applications for the sensor are described in more detail below.

The sensor further comprises a diaphragm assembly. The diaphragm assembly comprises a first diaphragm and a second diaphragm. The diaphragms are arranged to flex in response to changes in the pressure of the gas provided at the inlet. The first and second diaphragms are arranged to define a chamber therebetween, in particular by having the first and second diaphragms spaced apart. The first and second diaphragms are spaced apart a sufficient distance to allow both diaphragms to flex fully in response to the expected range of fluctuations in the pressure of the gas at the inlet.

In one embodiment, the diaphragm assembly comprises a housing, with the first and second diaphragms mounted at opposites ends thereof, the housing and the diaphragms defining the chamber. In one preferred arrangement, the housing is generally cylindrical, with the first and second diaphragms mounted at opposite ends of the cylindrical housing and defining a generally cylindrical chamber within the housing. The housing may be formed from any suitable material, most preferably an electrically conductive material, for example an electrically conductive metal.

In a preferred arrangement, the first and second diaphragms are arranged in the same orientation with respect to the chamber, in particular being parallel to one another, most preferably arranged on opposing sides of the chamber. In this way, deflection or movement caused by acceleration of the sensor or a change in position is the same in both diaphragms, allowing the effects of such movements on the output of the sensor to be reduced or negated.

The first and second diaphragms may have any suitable form. Suitable designs for diaphragms for pressure sensors are known in the art. Such aspects as the area of the diaphragm to be contacted by the gas, the thickness of the diaphragm and its material of construction will be determined by the range of pressure fluctuations to be measured. For example, for sensing small fluctuations in gas pressure, it is preferred to employ diaphragms that are thin and flexible, allowing the diaphragm to respond fully to the changes in gas pressure. When it is required to detect larger changes in the gas pressure, thicker and/or more rigid diaphragms may be employed.

The first and second diaphragms are most preferably of the same form. In particular, it is preferred that the first and second diaphragms both exhibit the same deflection and response to a given change in gas pressure within the chamber. In this way, the effects of orientation and movement of the sensor discussed above may be significantly reduced or cancelled by movement of the two diaphragms, leading to an improved quality of output signal from the sensor. This is achieved by having the first and second transducers arranged with an opposite polarity. In this way, movement of the first and second diaphragms in the same direction, such as arises under the actions of gravity or changes in orientation of the sensor, generates equal and substantially opposite signals from the transducers. These signals can be arranged to cancel one another, reducing or eliminating the effects of such movements. In contrast, movement of the first and second diaphragms in opposite directions, as arises due to pressure fluctuations within the chamber, generates two signals from the transducers, which can be summed. In this way, the sensor has a higher sensitivity to small movements of the diaphragms arising from pressure changes within the chamber.

The first and second diaphragms may be formed from any suitable material. Preferably, the first and second diaphragms are formed from the same material. As noted above, it is particularly advantageous that the amplifier, by being positioned in the chamber between the first and second diaphragms, can be shielded by the diaphragms. Accordingly, it is preferred that the first and second diaphragms are formed from a material that electrically shields the amplifier disposed therebetween, that is shields the amplifier from electrical and magnetic fields.

To improve shielding of the amplifier in the chamber, at least one of, more preferably both of, the first and second diaphragms are electrically grounded.

In embodiments in which the diaphragm assembly comprises a housing, the housing is preferably electrically grounded.

Suitable materials for forming the diaphragm are known in the art and are commercially available. Suitable materials include metals, in particular metal films. One preferred metal is brass. Alternative materials include polymers. It is preferred that the material of the diaphragm is electrically conductive, allowing the diaphragm to be grounded, as described above. In one embodiment, the diaphragm comprises a metallized polymer.

Each of the first and second diaphragms is provided with a transducer. The transducer is operable to convert movement of the respective diaphragm into an electrical signal. The first and second transducers are preferably in contact with the first and second diaphragms, respectively. Suitable transducers are known in the art.

A particularly preferred form of transducer is a piezoelectric transducer. Piezoelectric transducers suitable for use in the diaphragm assembly are known in the art and may be obtained commercially.

As noted above, each transducer is connected to a respective diaphragm. In one preferred embodiment, the diaphragm is constructed or formed to provide the piezoelectric transducer. For example, the diaphragm may comprise a plurality of layers across part or all of its surface, with a layer comprising a piezoelectric material. Suitable piezoelectric materials are piezo ceramics, more preferably metalized piezo ceramics. The piezoelectric material may be provided in a layer on part or all of the diaphragm, preferably being bonded to the diaphragm material. In one embodiment, the diaphragm and transducer comprises a conductive brass diaphragm having a layer of metalized piezo ceramic bonded thereto.

Alternatively, the diaphragm may be formed from a piezoelectric polymer. In this embodiment, the diaphragm and transducer are formed in a single component, with the piezoelectric polymer diaphragm flexing under the action of the changes in gas pressure within the chamber and generating an electrical signal as a result thereof. Preferably, the piezoelectric polymer is metalized in order to render it electrically conductive.

Suitable piezoelectric polymers, including piezoelectric polymer films, are known in the art.

The sensor of the present invention further comprises an amplifier. The amplifier is connected to the first and second transducers, receiving electrical signals from the transducers generated in response to movement of the respective diaphragm. As noted above, one advantage of the arrangement of the sensor is that, by having two diaphragms responsive to fluctuations in the gas pressure at the inlet of the sensor, the amplifier is provided with two signals representative of the pressure fluctuations, that is doubling the input of the amplifier, compared with an assembly having just a single amplifier.

A further advantage, also discussed above, is the ability to arrange the diaphragms such that the sensor has reduced sensitivity to movement, in particular acceleration, and to changes in orientation. Accordingly, the amplifier is preferably a differential amplifier, more preferably a differential amplifier with balance adjustment.

As noted above, it is preferred that the signal output by both diaphragms and transducers is the same in a reversed polarity, for a given change in the gas pressure within the chamber. A balance adjustment function within the amplifier allows for different responses of the two diaphragm/transducer assemblies to be corrected. In the case of a transducer based on a piezoelectric material, variations in the manufacturing process can result in two piezoelectric materials producing unequal electric charges in response to the same flexure. This inequality can result in the sensor being unable to completely cancel the effects of acceleration, for example arising from movement or a change of orientation of the sensor during use. By providing the differential amplifier with a balance adjustment, the amplifier may be operated to provide different gains to the two signals received from the first and second transducers, thereby compensating for the differences in signal output from the transducers. This balancing may be provided, for example by providing the differential amplifier with a potentiometer or its digital equivalent. The proper balancing of the differential amplifier may be determined by a simple test: the pressure sensor is rotated by 180° and the sensitivity of the sensor to acceleration due to gravity may be observed in a change to the signal output.

Suitable amplifiers and/or the components for constructing the amplifier are known in the art and are commercially available.

In use, the amplifier outputs an amplified signal representing the fluctuations in pressure in the gas within the chamber. The amplified signal may be fed to a processor, for example, to process and output data relating to the pressure fluctuations.

As noted above, the sensor has an inlet for a gas, with the inlet being connected to the chamber formed between the first and second diaphragms, such that fluctuations in the gas pressure in the chamber cause both the first and second diaphragms to flex. The chamber may be a sealed chamber, with only an inlet for gas.

Alternatively, the sensor is provided with an outlet for gas, with the outlet being connected to the chamber between the diaphragms. In use, the outlet may be open, allowing the chamber to vent to the atmosphere. In a preferred embodiment, the outlet is more restricted to the flow of gas than the inlet, for example has a smaller cross-sectional area for fluid flow. In this way, the outlet provides a minor path for the flow of gas out of the chamber, compared with the inlet. This in turn allows the chamber to vent slowly, for example to atmosphere. Such an arrangement ensures that the diaphragms respond fully to fluctuations in the pressure within the chamber, rather than the fluctuations merely increasing the flow of gas from the chamber through the outlet.

In use, the diaphragms flex in response to differences in gas pressure between the chamber and the gas external to the chamber and diaphragms, for example the atmosphere. In one application, the inlet of the chamber may be connected to receive a gas of fluctuating pressure to be measured. In this arrangement, the sensor provides an indication of changes in the pressure of the gas reaching the chamber, compared with the surrounding gas, for example ambient air. In an alternative application, the gas of fluctuating pressure to be measured may be provided to the exterior of the diaphragms, with the chamber connected via its inlet to a second body of gas, for example ambient air. In this way, the sensor will measure changes in the pressure of the gas surrounding the sensor and external to the diaphragms, with respect to the gas connected to the inlet of the chamber.

As described above, the amplifier is disposed within the chamber formed by the first and second diaphragms. In one preferred embodiment, the amplifier is mounted on a printed circuit board disposed in the chamber. The circuit board may be provided with one or more holes, such as openings or slots therein, to allow for the passage of gas therethrough.

As noted above, one use for the pressure sensor of the present invention is in a movement sensor assembly, in particular for detecting movements of the body of a person. Accordingly, in a further aspect, the present invention provides a movement sensor assembly for detecting movement of a person, the assembly comprising a flexible vessel containing a body of gas and a pressure sensor as hereinbefore described, the sensor being arranged to detect changes in the pressure of the gas within the flexible vessel.

The movement sensor assembly comprises a flexible vessel. Movement of the person causes the pressure within the flexible vessel to change. The pressure sensor is arranged to detect and measure these changes in pressure. In many embodiments, the pressure sensor is arranged to detect changes in pressure within the flexible vessel relative to a body of gas surrounding the flexible vessel, in particular ambient air.

In one embodiment, the inlet of the pressure sensor is connected to receive gas from within the flexible vessel, thereby allowing fluctuations in the pressure within the flexible vessel to change the pressure of gas within the chamber of the sensor. Alternatively, the sensor is exposed to the gas within the flexible vessel, such that the gas is external to the diaphragms of the sensor. In this way, changes in the gas pressure within the flexible vessel with respect to the gas within the chamber are detected by the sensor. In this arrangement, the chamber may be connected at its inlet to ambient air, for example. In one embodiment, the flexible vessel comprising an open celled foam therein, with the sensor placed within the open celled foam.

The movement sensor assembly of the pressure sensor may be employed in direct or indirect contact with the person. For example, the movement sensor assembly may be disposed with the flexible vessel in direct contact with the person, such that movement of the person is translated into flexing of the vessel wall, in turn causing the pressure of the gas within the vessel to fluctuate. Alternatively, movement sensor assembly may be in indirect contact with the person. For example, the flexible vessel may be disposed in or beneath a cushion or mattress, on which the person is sitting or lying.

It is an advantage of the present invention that the sensitivity of the pressure sensor is sufficiently high to allow very small movements of the person to be detected using the movement sensor assembly, in particular allowing the vital signs, such as the pulse and respiration rate, of the person to be detected and monitored.

Embodiments of the present invention will now be described, by way of example only, having reference to the accompanying drawings, in which.

Figure 1:
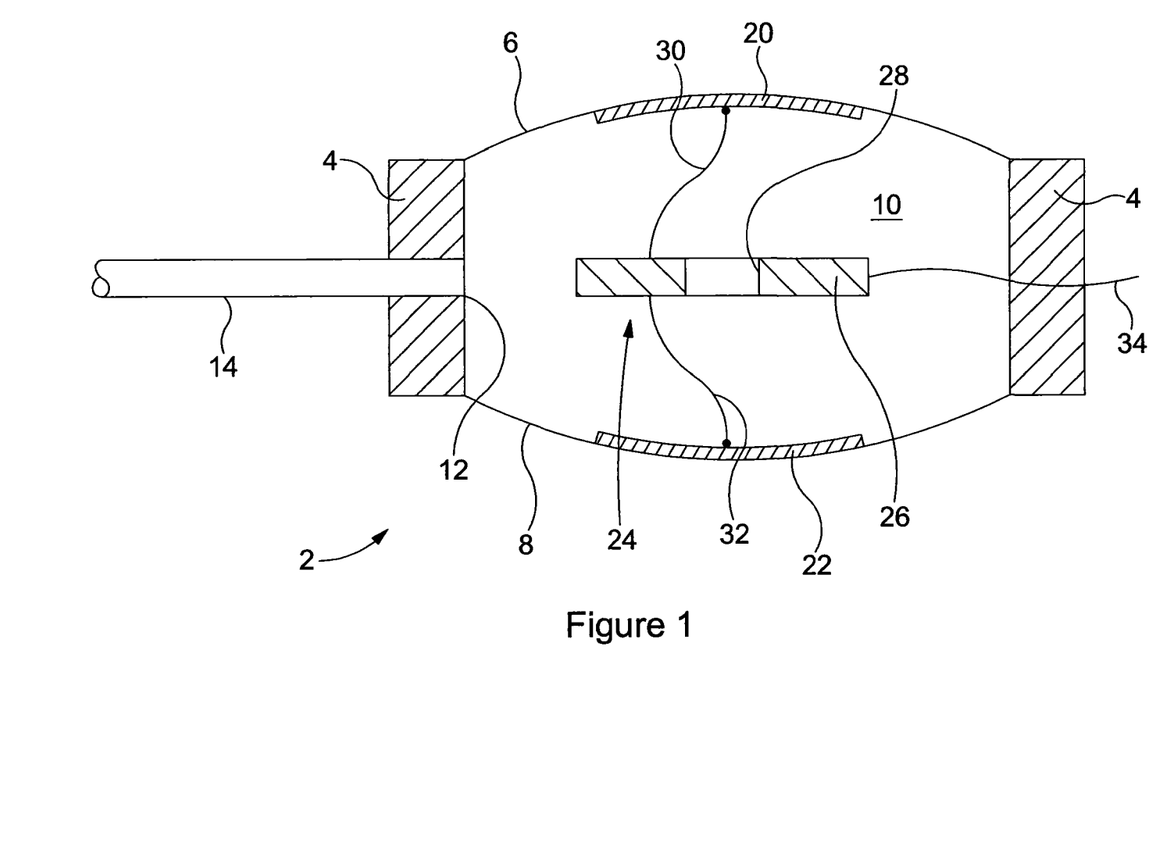
FIG. 1 is diagrammatical cross-sectional view of a pressure sensor according to one embodiment of the present invention.

Turning to FIG. 1, there is a shown a diagrammatical cross-sectional view of a pressure sensor according to a first embodiment of the present invention. The pressure sensor, generally indicated as 2, comprises a generally cylindrical housing 4. A first diaphragm 6 is mounted to one end of the housing 4 and a second diaphragm 8 is mounted to the other end of the housing 4. The first diaphragm 6 is bonded to the upper end of the housing 4 and forms an upper surface of the sensor 2, as viewed in the figure, while the second diaphragm 8 is similarly bonded to the lower end of the housing 4 and forms a lower surface.

The first and second diaphragms 6, 8 extend substantially parallel to one another and define therebetween a chamber 10. The first and second diaphragms 6, 8 are formed from a thin brass sheet and flex under the action of changes in the pressure of gas within the chamber 10. Each of the diaphragms 6, 8 is grounded.

The chamber 10 is provided with an inlet 12 in the forming of an opening in the housing 4, which is connected to a line 14. In use, the chamber 10 receives gas from the line 14 through the inlet 12.

Each of the first and second diaphragms 6, 8 is provided with a respective transducer. Each transducer comprises a sheet of piezo ceramic material 20, 22 bonded to the inner surface of the respective diaphragm 6, 8 by a suitable adhesive. In use, flexing of the diaphragms 6, 8 causes the respective piezo ceramic sheet to flex, as shown in FIG. 1.

An amplifier 24 is provided on a circuit board 26 mounted centrally in the chamber 10 between the first and second diaphragms 6, 8. The circuit board 26 is provided with an opening 28 therein, to allow the passage of gas therethrough.

The amplifier 24 is connected to each of the transducers 20, 22 by respective leads 30, 32.

Leads 34 extend from the amplifier 24 through the housing 4 to supply electrical power to the amplifier and to carry electrical signals output by the amplifier, for example to a suitable display and/or recording device.

A lead 34 extends from the amplifier 24 through the housing 4 to carry an electrical signal output by the sensor 2.

In operation, the line 14 is connected to a source of gas, fluctuations in the pressure of which are to be measured. The chamber 10 is filled with gas. Fluctuations in the pressure of the gas are communicated to the interior of the chamber 10. These fluctuations cause the first and second diaphragms 6, 8 to flex, in particular to flex outwards in response to increases in the gas pressure, as shown in FIG. 1, and to flex inwards in response to reductions in the gas pressure. Flexing of the first and second diaphragms 6, 8 in turn flexes the respective transducers 20, 22, generating an electrical signal from each. The electrical signals are amplified by the amplifier 24 and a signal corresponding to the change in gas pressure output along the line 34.

Figure 2:
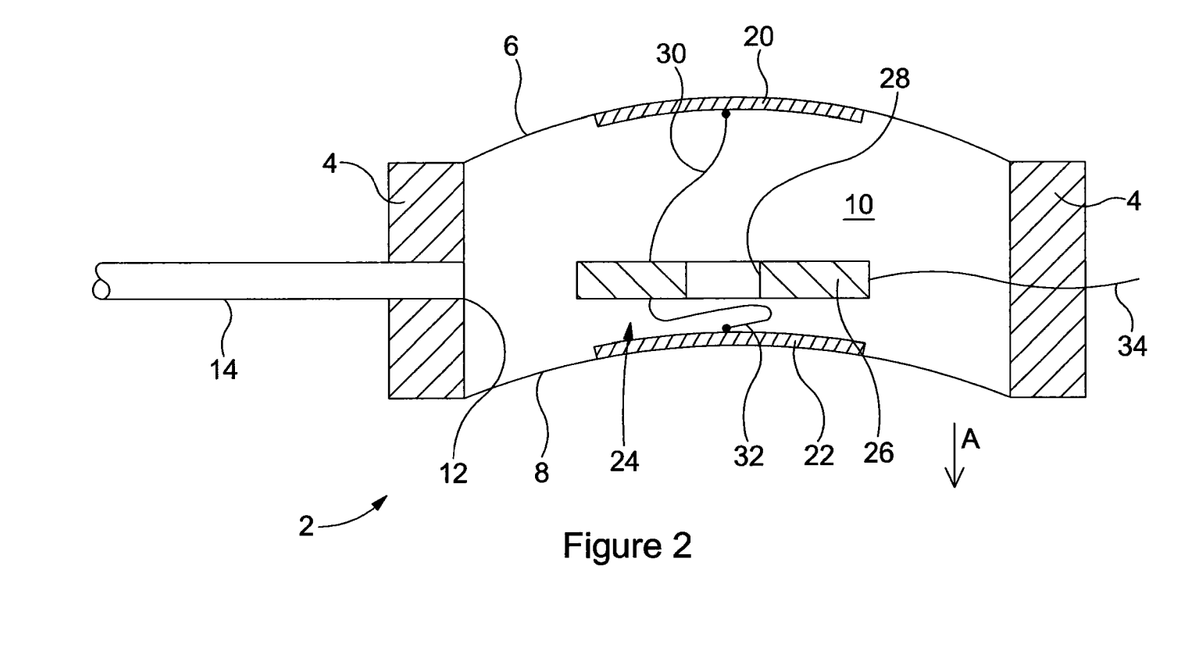
FIG. 2 is a diagrammatical cross-sectional view of the sensor of FIG. 1 when subjected to a downwards acceleration.

The diaphragms 6, 8 are arranged on opposing sides of the chamber 10, as shown in FIG. 1. In this way, movement of the diaphragms as a result of movement or a change in position of the sensor produces a net signal output of zero, that is the flexing of the diaphragms and the transducers cancels one another. In this way, the sensitivity of the sensor to acceleration due to movement is reduced or eliminated. This is illustrated in FIG. 2. In FIG. 2, the sensor of FIG. 1 is shown subjected to an accelerated downwards motion, indicated by the arrow A. As can be seen, the first diaphragm 6 is flexed upwards, as viewed in FIG. 2, that is outwards from the chamber 10. The second diaphragm 8 is also flexed upwards, as viewed in FIG. 2, that is inwards into the chamber 10. The transducers 20, 22 are caused to flex in opposite manners by this flexing of the diaphragms and produce signals of opposite polarity, allowing the signals from the transducers to cancel one another.

Figure 3:
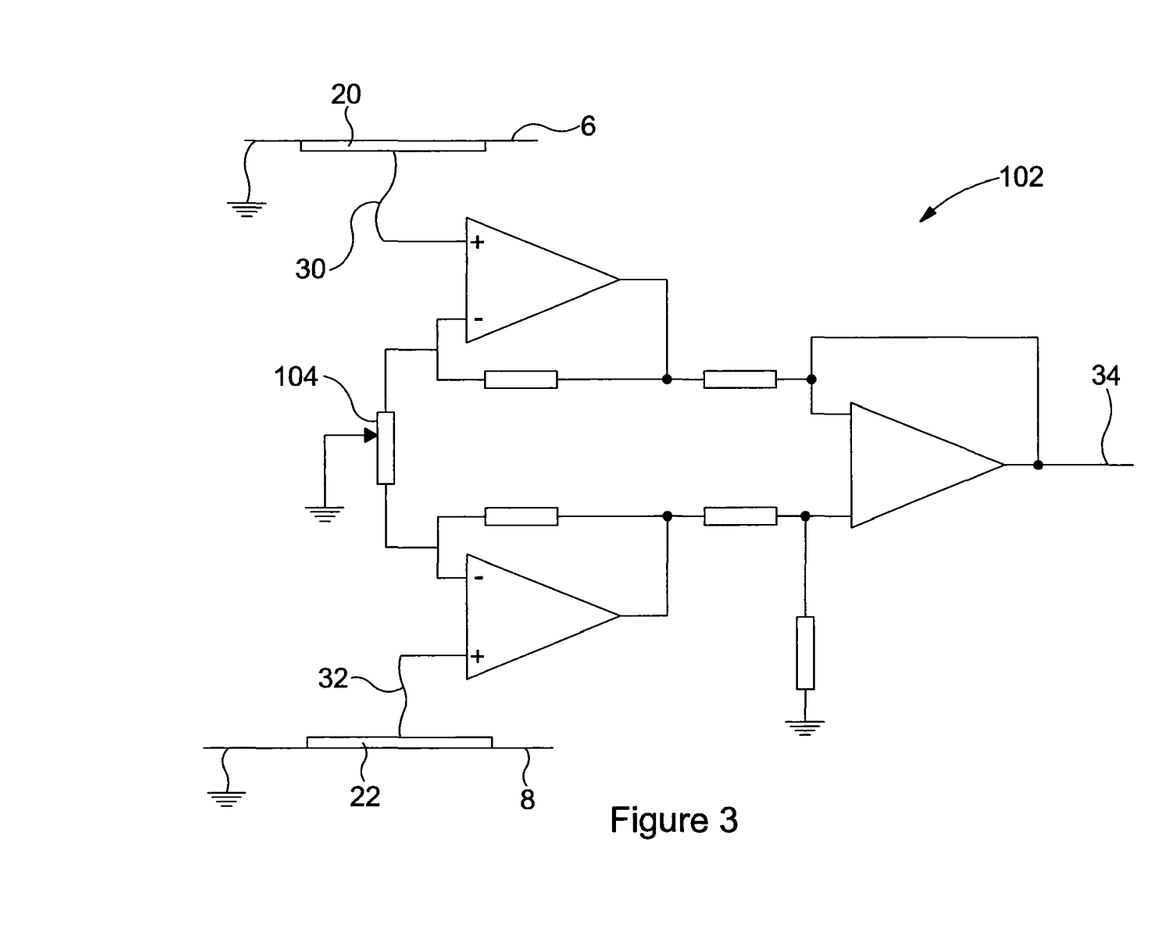
FIG. 3 is a circuit diagram of a differential amplifier for use in the pressure sensor of FIG. 1.

The amplifier 24 is a differential amplifier, that is amplifies the difference between the signals received from the transducers 20, 22. The circuit diagram of one example of a suitable differential amplifier is shown in FIG. 3. The differential amplifier 102 comprises a balance adjustment facility, by way of potentiometer 104, to allow differences in the output of the transducers 20, 22 to be accommodated.

As noted, the transducers 20, 22 have opposite polarities, that is movement of the first and second diaphragms 6, 8 in the same direction, either upwards or downwards as viewed in the figures, causes the transducers 20, 22 to generate electrical signals that substantially equal in magnitude but opposite in polarity. In this way, flexing of the diaphragms 6, 8 in the same direction as shown in FIG. 2, for example, arising for example due to movement of the sensor downwards as viewed in the figure, generates two equal and opposite signals from the transducers 20, 22, which cancel each other and generate no output signal from the sensor. In contrast, flexing of the diaphragms 6, 8 in opposite direction as shown in FIG. 1, arising from an increase in pressure within the chamber, generates two equal signals from the transducers 20, 22 of the same polarity, which are summed in the amplifier, to provide an increased sensitivity to pressure fluctuations within the chamber.

Figure 2A:
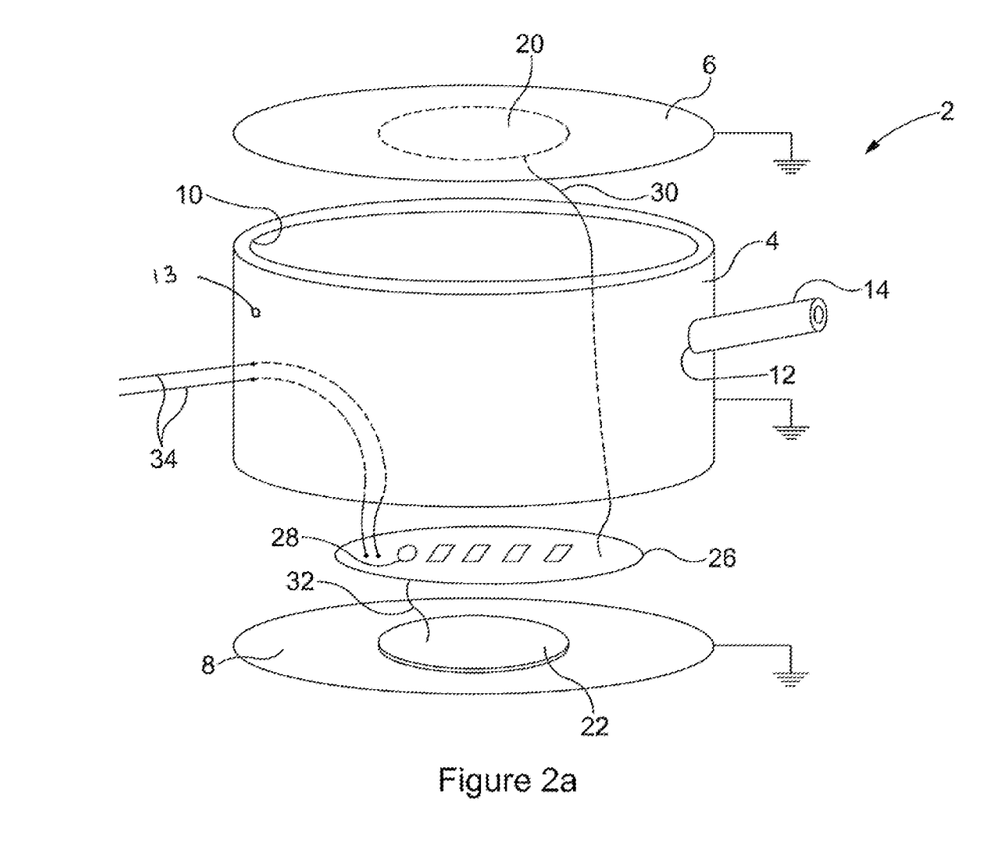
FIG. 2a is an exploded diagram of the pressure sensor of FIG. 1, to show the component parts.

FIG. 2a further shows an optional outlet 13 connected to the chamber. The gas flow path provided by the outlet may be smaller than the gas flow path provided by the inlet.

Figure 4:
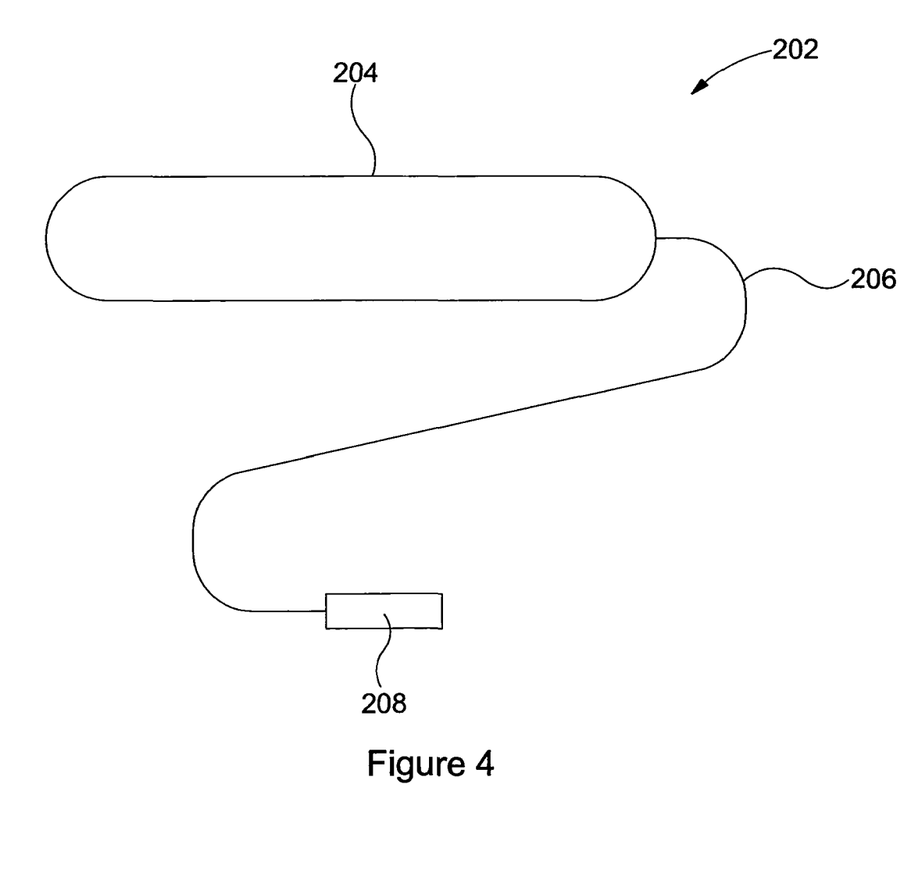
FIG. 4 is a diagram of a movement sensor assembly of the present invention.

Finally, turning to FIG. 4, there is shown a movement sensor assembly, generally indicated as 202. The assembly comprises a flexible vessel 204 holding a reservoir of gas therein. The flexible vessel 204 may be provided, for example, by an inflatable pillow, cushion or mattress on which a user may sit or lie. A line 206 connects the interior of the vessel 204 to the chamber of a pressure sensor 208 of the present invention. The pressure sensor 208 may be of the arrangement shown in FIGS. 1 and 2 and described above.

In use, movement of the user generates increases or decreases in the pressure of the gas within the vessel 204. These changes in gas pressure are communicated to the pressure sensor 208 via the line 206. The pressure sensor 208 generates an electrical signal corresponding to the changes in gas pressure and indicating movement of the user.

The invention claimed is:

1. A pressure sensor comprising:
   an inlet for connecting to a body of gas;
   a diaphragm assembly comprising:
   a first diaphragm and a second diaphragm, the first and second diaphragms defining a chamber therebetween, the chamber being connected to the inlet;
   a first transducer responsive to movement of the first diaphragm and operable to produce a first electrical signal in response to the same; and
   a second transducer responsive to movement of the second diaphragm and operable to produce a second electrical signal in response to the same; and an amplifier disposed in the chamber of the diaphragm assembly and connected to the first and second transducers to receive the first and second electrical signals therefrom.

2. The pressure sensor according to claim 1, wherein the diaphragm assembly comprises a housing, the chamber being defined by the first and second diaphragms and within the housing.

3. The pressure sensor according to claim 2, wherein the housing is formed from an electrically conductive material.

4. The pressure sensor according to claim 1, wherein the first and second diaphragms are arranged in the same orientation with respect to the chamber.

5. The pressure sensor according to claim 1, wherein the first and second diaphragms are of the same form, so as to flex the same amount in response to a given fluctuation in gas pressure.

6. The pressure sensor according to claim 1, wherein the first and second diaphragms are formed from the same material and wherein the material electrically shields the amplifier in use.

7. The pressure sensor according to claim 1, wherein each of the first and second transducers is in contact with the respective diaphragm.

8. The pressure sensor according to claim 1, wherein the first and second transducers are piezoelectric transducers.

9. The pressure sensor according to claim 8, wherein the first and second transducers each comprise a layer of piezo ceramic material.

10. The pressure sensor according to claim 1, wherein the first transducer is arranged to output a first signal in response to a flexing of the first diaphragm in a first direction and the second transducer is arranged to output a second signal in response to flexing of the second diaphragm in the first direction, the first signal having an opposite polarity to the second signal.

11. The pressure sensor according to claim 1, wherein the first diaphragm and transducer and the second diaphragm and transducer are arranged to output signals of substantially the same magnitude in response to a fluctuation in the pressure of a gas being measured by the sensor.

12. The pressure sensor according to claim 1, wherein the amplifier is a differential amplifier.

13. The pressure sensor according to claim 1, wherein the chamber further comprises an outlet for gas.

14. The pressure sensor according to claim 13, wherein the gas flow path provided by the outlet is smaller than the gas flow path provided by the inlet.

15. A movement sensor assembly for detecting movement of a person, the assembly comprising a flexible vessel containing a body of gas and a pressure sensor according to claim 1, the sensor being arranged to detect changes in the pressure of the gas within the flexible vessel.

16. The movement sensor according to claim 15, wherein the pressure sensor is arranged to receive gas from within the flexible vessel to an exterior of the first and second diaphragms.

* * * * *